(12) United States Patent
Mangena

(10) Patent No.: US 6,653,469 B1
(45) Date of Patent: Nov. 25, 2003

(54) ANTIBIOTIC PURIFICATION METHOD

(75) Inventor: Murty Mangena, Lexington, KY (US)

(73) Assignee: Murty Pharmaceuticals, Inc., Lexington, KY (US)

(*) Notice: Subject to any disclaimer, the term of this patent is extended or adjusted under 35 U.S.C. 154(b) by 0 days.

(21) Appl. No.: 10/176,193

(22) Filed: Jun. 20, 2002

(51) Int. Cl.⁷ .......................... C07D 267/22; C07C 7/00
(52) U.S. Cl. ....................................... 540/468; 585/800
(58) Field of Search ........................... 540/468; 585/800

(56) References Cited

U.S. PATENT DOCUMENTS

| | | | |
|---|---|---|---|
| 3,595,955 A | * 7/1971 | De Boer | .................... 424/121 |
| 5,188,945 A | 2/1993 | Carter et al. | |
| 5,591,438 A | 1/1997 | Olson et al. | |
| 5,942,611 A | 8/1999 | Borden et al. | |

OTHER PUBLICATIONS

Neckers, "Geldanamycin as a potential anti–cancer agent: Its molecular target and biochemical activity", Investigational New Drugs 17: 361–373, 1999, Kluwer Academic Publishers, the Netherlands.

Supko, "Preclinical pharmacologic evaluation of geldanamycin as an anti–tumor agent", Cancer Chemother Pharmacol (1995) 36: 305–315, Springer–Verlag 1995.

De Boer, "Geldanamycin, a new Antibiotic", The Journal of Antibiotics, vol. XXIII, No. 9, 442–447, Sep. 1970.

* cited by examiner

*Primary Examiner*—Elli Peselev

(57) ABSTRACT

Taught is a process for purifying a benzoquinoid ansamycin antibiotic such as geldanamycin through the use of a fluid comprising supercritical carbon dioxide. In certain embodiments the fluid also includes an aliphatic alcohol such as methanol or ethanol.

23 Claims, No Drawings

ANTIBIOTIC PURIFICATION METHOD

STATEMENT REGARDING FEDERAL SPONSORSHIP

Because at least a portion of what is described below was sponsored under a federal contract, the federal government may retain certain rights in the invention.

FIELD OF THE INVENTION

The invention relates to an antibiotic purification method.

DESCRIPTION OF THE RELATED ART

Antibiotic sales total billions of dollars per year, and have increased. Antibiotics are prepared from biological sources by extraction; by chemical synthesis; or by a combination of these methods. Because of the large market for antibiotics, there is a long-felt need for improved methods of recovering antibiotics from biological sources. An improved method may possess any one or more of the following features (presented by way of example and not of limitation): lower cost; greater yield; greater purity of the final product; use of starting materials or reagents that are more readily available; production of less harmful waste-stream or by-products; etc.

While antibiotics are thought of as means to control infectious disease, antibiotics are also useful in the treatment of chronic disease such as cancer. In particular, certain classes of antibiotics which are cytotoxic to certain cancer cells, and hence are useful as antineoplastic chemotherapeutic agents, are either in use or under active investigation as anticancer pharmaceuticals. See generally Remers, William A., The chemistry of antitumor antibiotics, Vols. 1 & 2 (1979, 1989). There are several quinone-containing agents which cause DNA damage and which have therefore been useful as antineoplastic agents. See Begleiter, A., Clinical applications of quinone-containing alkylating agents. Frontiers in Bioscience 5, e153–171 (2000). However, there has been interest in other agents which might act against other cellular targets, such as heat shock protein 90 (Hsp90). Hsp90 is a chaperone protein that has been found to be associated with cell proliferation proteins, such as certain protein kinases. Hsp90 is found at higher levels in tumor cells than in normal cells. Members of the benzoquinoid ansamycin class of drugs, such as geldanamycin, herbimycin A, and macbecin II, have been shown to bind specifically to Hsp90 and affect Hsp90 function, and are regarded as first generation Hsp90 antagonists. Among the benzoquinone ansamycins, geldanamycin in particular has been recognized and studied as an Hsp90 inhibitor. Because Hsp90 and similar proteins are regarded as targets for antineoplastic chemotherapy, geldanamycin's effectiveness at inhibiting tumor growth has been studied, with results showing 13 nM geldanamycin achieving growth inhibition of 50% in highly responsive cell lines. There has therefore been interest in preparation and purification of geldanamycin for laboratory or clinical study. See generally Neckers, L., et al. Geldanamycin as a potential anti-cancer agent: Its molecular target and biochemical activity. Investigational New Drugs 17: 361–373 (1999).

Antibiotics tend to have complex structures, making their total synthesis somewhat difficult. When a large market has not yet been established for an antibiotic, it is not necessarily cost-effective to produce an antibiotic routinely by total synthesis. Instead, the antibiotic may be prepared by extraction from a biological source or, in some cases, semisynthetically.

Therefore it is known in the art that certain antibiotics can be recovered from fermentation broths. See, for example U.S. Pat. Nos. 5,188,945; 5,591,438; 5,942,611.

In the art, the benzoquinoid ansamycin antibiotic geldanamycin has been prepared from the culture filtrate of *Streptomyces hygroscopicus* var. *geldanus* var. *nova*, through the use of an initial butanol extraction followed by subsequent steps employing the halogenated organic solvent chloroform. Geldanamycin has been shown to be soluble in alcohols and aliphatic chlorinated solvents such as chloroform; to be less soluble in acetone, benzene, and ethyl acetate; to be only slightly soluble in water; and to decompose easily with acid, base, or heat in the presence of oxygen. See DeBoer, C., et al. Geldanamycin, a new antibiotic. J. Antibiot. 23, 442 (1970). Geldanamycin also undergoes photolytic degradation in both aqueous and nonaqueous solutions. See Supko, J. G., et al., Preclinical pharmacologic evaluation of geldanamycin as an antitumor agent. Cancer Chemother Pharmacol 36: 305–315 (1995).

There may be certain limitations to extractions that rely on halogentated organic solvents. Certain halogenated organic solvents such as chloroform may be regarded as hazardous materials and hence may give rise to a wastestream containing hazardous materials and may need to be thoroughly removed from an end-product that might be administered to humans.

Commonly used liquid-solid extraction processes may employ the Soxhlet apparatus. Such processes may take a long time and produce high-volume, dilute solutions which typically must be concentrated.

On the basis of the art it can be seen that it might reasonably be desired to devise a method for recovering a benzoquinoid ansamycin antibiotic from a fermentation broth, which method does not rely on halogenated organic solvents and which method does not needlessly subject the desired product, geldanamycin, to degradation due to acid, base, or heat.

DETAILED DESCRIPTION OF THE INVENTION

The present invention provides inter alia a process for purifying a benzoquinoid ansamycin antibiotic, said process comprising contacting a mixture comprising the antibiotic with a fluid comprising supercritical carbon dioxide.

The present invention also provides inter alia a process for purifying a benzoquinoid ansamycin antibiotic from a fermentation broth that contains the antibiotic, said process comprising (a) separating the fermentation broth into a particulate phase and a liquid phase, and (b) extracting the antibiotic from the particulate phase.

The present invention also provides inter alia geldanamycin purified by a process comprising contacting a mixture comprising geldanamycin with a fluid comprising supercritical carbon dioxide.

As used in connection with the present invention, "purifying" means substantially separating a desired composition from a mixture that contains not only the desired composition but also at least one other composition. For example, evaporation is a process for purifying sodium chloride from an aqueous solution of sodium chloride. In this example, after evaporation, that is, after the process for purifying sodium chloride has been performed, the desired sodium chloride is obtained substantially free of water. However, a relatively small quantity of water may yet remain with the desired sodium chloride even after the process has been performed. Therefore, purifying results in a composition's being separated from at least one other composition in a mixture but need not result in a composition's being separated from every molecule of every other composition in the mixture. For example, crystallization is a process for purifying a desired composition that can form a crystalline solid from a mixture that contains not only the desired composition but also a crystallization solvent and an impurity. The crystalline solid obtained by crystallization may contain relatively small amounts of the crystallization solvent and may also contain relatively small amounts of the impurity.

As used in connection with the present invention, "extracting" means contacting a matrix with a fluid, wherein said contacting transfers a desired composition from the matrix to the fluid.

In seminal work concerning the benzoquinoid ansamycin antibiotic geldanamycin, DeBoer, C., et al. Geldanamycin, a new antibiotic. J. Antibiot. 23, 442 (1970), the filtrate of S. hygroscopicus culture medium was extracted with butanol to recover impure geldanamycin. Subsequent steps in the DeBoer work included crystallization, dissolution of the crystals in chloroform, filtration, and another crystallization. In later work performed by other investigators at the National Cancer Institute (NCI) Frederick Cancer Research and Development Center, lot #100904 was prepared by initial steps including centrifugation of the whole broth and extraction of the supernatant with ethyl acetate, the solids resulting from the centrifugation of the whole broth being discarded.

In part on the basis of the results of preparation of lot #100904, it was recognized in the art that existing methods of recovering geldanamycin from fermentation broth were inadequate. Moreover, on the basis of the DeBoer work and that of NCI, the art taught away from recovering geldanamycin from the solids resulting from the centrifugation of the whole broth.

In all the following examples except "Example: Process including SCF and organic solvent extractions," the fermentation broth was a broth in which the producing organism was S. hygroscopicus var. geldanus.

Example: Geldanamycin Extraction from Fermentation Broth. The initial trial run was intended to evaluate the SCF extraction method with and without co-solvents, and also to separate the liquids and solids from the fermentation broth. One liter of fermentation broth (MPI Lot #01-139, Mfg. #253009) was placed into a one-liter beaker. The beaker was placed in refrigerator for 24 hours to allow the solids to separate from liquid. The broth was filtered with 0.8 $\mu$m filter papers (lot #01-130 followed by Whatman filters, Mfg. #709504 due to clogging). The top layer was filtered leaving the bottom layer for easy filtration and eventually all 1 liter contents were filtered. During the filtration, several filters were used and they were separated into two sets: clean and dark filters. The two sets of filtered papers were then extracted through the SCFE.

For the first SCFE trial run using clean yellow filters, only liquid carbon dioxide was used as the solvent and the SCFE was run at 35° C. and 200 bar. A negligible quantity of solids was extracted. The sample was labeled SCF Extract #1. The SCFE was set up again and 100 mL of ethanol was used as the co-solvent and ran at 35C and 200 bar. The sample taken out was yellowish. The sample was labeled R010807 ethanol extract #1 (EtOH 1). The SCFE was set up again at 35° C. and 400 bar. The sample obtained was labeled as ethanol extract #2 (EtOH 2). The SCFE was set up to run at 40° C. and 400 bar and 100 mL of ethanol was used as the co-solvent. Samples were collected at 30-minute intervals for one hour. The sample was labeled as R010807 ethanol extract #3 (/EtOH 3).

These filters were then extracted in a conical flask using ethyl acetate in order to ascertain whether any residual geldanamycin remained on the filters. The extracted filters were placed in a conical flask after being cut into smaller pieces. A sufficient quantity of ethyl acetate was added to cover all the filters. The flask was corked and wrapped with aluminum foil. The contents were placed on a shaker for 24 hours for mixing. The material was taken out and labeled as ethyl acetate extract #1 (R010807 EtOAc #1). All samples were analyzed by HPLC to determine the quantity of geldanamycin. The results are presented in Table 1.

The other set of filters, the dark set, were extracted through the SCF system with 100 mL of methanol as the co-solvent. The SCFE was set up at 40° C. and 400 bar. Samples were taken every fifteen minutes for two hours. Fifty-six mL of sample was collected by the end of the run and it appeared yellow in color. The sample was labeled as R010807 methanol extract #1A (R010807 #1A, MeOH). The filters were extracted a second time under the same conditions. The sample was yellow again and a total of 58 mL was collected. The sample was labeled as R010807 methanol extract #2A (R010807 #2A, MeOH). The same filters were again subjected to the SCFE process at 40° C. and 400 bar using 100 mL of methanol as co-solvent. Samples were taken every fifteen minutes. The cumulative sample totaled 56 mL, was light yellow in color and was labeled as R010807 methanol extraction #3A (R010807 #3A, MeOH), The same procedure was once again repeated and 58 mL was collected. The sample was more light yellow than extraction #3A. The sample was labeled as R010807 methanol extraction #4A (/R010807 #4A). The SCF extracted filters were cut up into smaller pieces and placed in a conical flask with sufficient ethyl acetate to cover the filters. The flask was corked and covered with aluminum foil. The flask was connected to a shaker and the filter paper pieces were mixed for 24 hrs. The material was labeled as R010807 Ethyl Acetate #2 (R010807 EtOAc #2). All samples were analyzed by HPLC to determine the quantity of geldanamycin. The results are presented in Table 1.

The filtrate obtained from the above filtration (R010807) was kept in the refrigerator to allow for additional settling of solids. Due to the resulting settling, the contents were again centrifuged by filling the centrifuge tubes up to the 30 mL mark. The contents were then centrifuged for fifteen minutes at 3600 RPM. After centrifugation, the top layer was decanted and placed in a 1000-mL beaker. The solids were left in the centrifuge tubes and placed inside the refrigerator until further processing. The supernatant was labeled as R010807 Sup. #1.

The solids from the bottom of the centrifuge tubes (R010807) were mixed with glass beads (lot #01-129). The solids were then collected on filter paper and extracted through the SCFE at 40° C. and 400 bar. 100 mL of methanol was used as the solvent. The sample was labeled as methanol extract #1 after centrifugation (/R010807 #1, MeOH). The sample was placed in the refrigerator. The same procedure was repeated for methanol extract #2 after centrifugation (/R010807 #2, MeOH). The sample was light yellow in color. All samples were analyzed by HPLC to determine the quantity of geldanamycin. The results are presented in Table 1.

After the HPLC analysis, all methanol samples obtained from (R010904) were pooled in one container and stored in the refrigerator for further processing.

This example establishes that SCF extraction of geldanamcycin requires a co-solvent of either methanol or ethanol. Moreover, when extraction is conducted in this manner, the geldanamycin is present mostly in the solids rather than the liquid portion of the fermentation broth. Finally, the separation of the solids from the liquid is more efficient by centrifugation rather than filtration.

Example: Geldanamycin SCF Extraction from Fermentation Broth. One liter of fermentation broth (01-139) was placed in a 1000-mL beaker and set in the refrigerator in order to separate solids from the liquid portion. The broth for lot #R010904 was decanted and placed in eight different centrifuge tubes and were centrifuged for fifteen minutes at 3600 RPM repeatedly by decanting the supernatant and filling with fresh broth. The bottom layer that had settled in the beaker was also centrifuged. The solutions in the centrifuge tubes were decanted and placed in a 1000-mL beaker. The solids (pellets) were left in the centrifuge tubes. The decanted clear supernatant was labeled R010904 Sup #1. The cloudy supernatant still contained solids and was kept in the refrigerator for further settling. It was again centrifuged and the solids were collected. The supernatant was labeled R010904 Sup #2, which was slightly cloudy due to the presence of some amount of solids.

All the solids left at the bottom of the centrifuge tubes were mixed with 3 mm glass beads. The beads were then placed in the sample holder of the SCFE for extraction. The sample holder was placed in the refrigerator for SCF extraction. The SCFE was set at 400 bar and 400° C. The glass beads along the solids were extracted with no co-solvent (carbon dioxide alone) for one hour. There was a yellowish solid (1.4 g) in the sampling vessel at the end of the run. The sample was labeled as R010904 extraction #1 (/R010904 semisolid).

The SCFE was run again at 400 bar and 40° C. with 100-mL methanol to clean out the system without the coated beads. The sample was initially yellow in color and eventually became lighter and 60-mL of sample was collected. Samples were collected every fifteen minutes hereafter and the pooled sample was labeled as R010904 methanol extraction #2 (R010904 #2, MeOH).

The glass beads were placed back in the SCFE. The SCFE was set up at 400 bar and 40° C. and 100-mL of methanol was used as the co-solvent. The same procedure was repeated six more times (R010904 #8, MeOH).

The SCFE was again set at 400 bar and 40° C. to extract the same glass beads. The centrifuge tubes and the containers that were used for centrifugation and separation of solids were rinsed with 100-mL methanol in order to collect any adhered solid materials. The washed methanol was then used as the co-solvent for extraction with the glass beads. A total of five more extractions were done under the same conditions with 100-mL of fresh methanol for each extraction. The samples were collected separately for each extraction. All samples were analyzed by HPLC to determine the quantity of geldanamycin. The results are presented in Table 2.

Example: Processing of SCFE Solvent Samples to Crystallize Geldanamycin. The methanol samples from both R010807 and R010904 were pooled into one container and sampled to estimate the quantity of geldanamycin. The methanol samples were then filtered and sampled again. These samples were analyzed by HPLC. The sample before filtration contained 418.6 ug/mL and sample after filtration contained 401.9 ug/mL.

A small quantity of solids was obtained during initial filtration and they were labeled as R010807-1, R010904-1. The filtrate was then placed onto a rotary evaporator to distill the solvent and increase the concentration of the geldanamycin to precipitate/crystallize the product. The rotary bath temperature stayed between 20° C. and 25° C. The slurry was filtered with qualitative Whatman #1 filter paper (lot #709504). The solids were collected and labeled as R010904-2, R010807-2. The filtrate was re-filtered with Whatman #42 filter paper (lot #1600). The solid was collected and labeled as R010807-3, R010904-3. The filtrate was then placed in the freezer (approx. −20° C.) overnight.

The next day, the filtrate was re-filtered with the same #42 filter paper that was used previously. The solids were collected and labeled as (R010807-4, R010904-4). The filter paper was then dried and more solids were collected. They were labeled as (R010807-5, R010904-5). The samples, filter paper, and filtrate were placed inside a vacuum desiccator. The left out filtrate at the end of distillation/crystallization was labeled as filtrate-1 (R010807, R010904). The amount of product obtained by precipitation/crystallization is as follows: R010807R010904-1, about 16 mg; R010807R010904-2, about 201 mg; R010807R010904-3, about 157 mg; R010807R010904-4 about 42 mg; R010807R010904-5, about 24 mg. These products were analyzed by HPLC to determine the purity of the geldanamycin. The purity results of these materials are presented in Table 3.

These efforts resulted in the extraction of the geldanamycin from fermentation broth using a co-solvent and initiation of purification of the compound from the extracted solvent by distillation at room temperature. The purity of the final product ranged from 12.9% to 96.6% depending on the stage of separation.

Example: SCF Extraction of Geldanamycin from Fermentation Broth Using a Co-solvent. In this example, batch size was increased to two liters of broth (MPI Lot #01-139, Mfg. #253009). It was placed in a measuring cylinder to separate the solids from the liquid. The broth was allowed to settle in the refrigerator for one week. The floating material on top was transferred into one centrifuge tube. The clear liquid layer was centrifuged followed by the bottom portion containing more solids. The broth in the tubes was centrifuged for 20 minutes at 3600 RPM. The supernatant was transferred into two 1000mL beakers leaving the solid pellet behind in the tubes. The solid pellets at the bottom of the centrifuge tubes were pooled into two tubes and re-centrifuged. The liquid was decanted and the pellet left at the bottom was mixed with the recycled (washed) glass beads used for Lot#s R010807, R010904. The glass beads were then placed into the SCF extraction basket. The decanted supernatant was re-centrifuged again to collect additional solids and the pellet at the bottom was mixed with more glass beads and placed in the SCF extraction basket. This procedure was repeated until all the solids were collected.

The SCFE was set at 400 bar with carbon dioxide at a flow rate 20 g/min and 40° C. Cosolvent was not used for the first run. The run lasted for two hours and 30 minutes. About 2.84 g of semi-solid material was collected at the end of the extraction. The sample was labeled as extraction #1R011001 (/R011001 semisolid).

The beads were then taken out and 100 mL of methanol was placed inside the sample holder. A second run was conducted under the same conditions to wash the system. The run lasted one hour and samples were taken every five minutes. About 77 mL of solvent sample was collected at the end of the run. The sample was light yellow at first and then clear at the end. The sample was labeled as MeOH extract #2 R011001 (MeOH 2).

The beads were placed back in the sample holder and a third run was conducted under the same conditions. Methanol (100 mL) was used to rinse the centrifuge tubes and the 1000-mL beakers that were used to collect solids, which adhered to the contact surfaces of the containers. This methanol was used as the co-solvent to extract the geldanamycin. Samples were taken every five minutes and 86-mL was collected at the end of the run. The sample was a thick-dark-yellow liquid. The sample was labeled as MeOH extract #3 R011001 (/MeOH 3).

The SCFE was set up again under the same conditions and 100-mL of methanol was used as the co-solvent. Nearly 64 mL was collected and the sample was a dark-yellow liquid. The sample was labeled as MeOH extract #4 R0011001 (MeOH 4). This procedure was repeated until the sample was clear (MeOH #22) with the addition of 100 mL for each run.

The beads were taken out and the SCFE was run again under the same conditions for leaning purposes. The sample was dark yellow at first and turned clear at the end.

Nearly 61 mL of solvent sample was collected at the end of the washing. The sample was labeled as 'Cleaning sample'. All samples were analyzed by HPLC to determine the quantity of geldanamycin. The results are presented in Table 4.

About 1.6 liters of the centrifuged broth (supernatant) was sent to Compact Membrane Systems, Inc. for osmotic distillation (OD) to concentrate the supernatant and to recover any geldanamycin present in the concentrate by SCFE. The supernatant was concentrated to approximately 55 mL by OD and was returned (MPI Lot #01209). The concentrate along glass beads was subjected to SCFE at 375 bar, 20 g carbon dioxide/min., and 40° C. for 1 hour. Two mL of light yellow liquid sample was collected at the end of the run. The sample was labeled as osmotic distillation extract #1 (/Osmotic Diss. 1). The next extraction was done using 100 mL of methanol as the co-solvent. Approximately 80 mL of sample was collected and the sample was a light-yellow liquid. The sample was labeled osmotic distillation extract #2 (Osmotic Diss 2). The third run was conducted under the same conditions. The sample was light yellow and 75 ml, was collected at the end of the run. The sample was labeled as osmotic distillation extract #3 (/Osmotic Diss. 3). All samples were analyzed by HPLC to determine the quantity of geldanamycin. The results are presented in Table 4. The OD sample analysis showed that a negligible quantity of Geldanamycin was recovered from the supernatant.

The methanol samples were filtered using Whatman filter paper #42 (lot #1600). The solids were collected and labeled as R011001-1. The filtrate was then concentrated using a rotary evaporator. The rotavap bath temperature was maintained between 20° C. and 25° C. The concentrated slurry was placed in the refrigerator overnight. The next day, the slurry was filtered and the solids were collected and labeled (R011001-2). The filtrate was transferred back into the rotary flask and swirled to collect the solids sticking to the surface and the solution was filtered again to separate the solids. These samples were labeled as (R011001-3). The filtrate was then placed on a rotary to evaporate more solvent. The solvent was evaporated until the solution turned into slurry. The slurry was placed into the freezer (−20° C.) for three hours. The slurry was filtered and the solid was collected and labeled as R011001-4. The filtrate was placed on a hot plate overnight and then on a vacuum desiccator.

The filtrate was labeled as filtrate-2 (R011001). The amount of crystallized final product was as follows: R011001-1, 84 mg; R011001-2, 268 mg; R011001-3, 97 mg; R011001-4, 429 mg. All samples were analyzed by HPLC to determine the quantity of geldanamycin. The results are presented in Table 5. The results showed that the purity of the Geldanamycin ranged from 9.1% to 85.7% depending on the stage of separation.

Example: Selective SCF Extraction of Geldanamycin from Fermentation Broth Using Methanol as Co-Solvent. Approximately 2.2 liters of the geldanamycin broth (lot #01-139) was placed into a measuring cylinder. The cylinder holding the broth was placed in the refrigerator for one week to separate the solid from the liquid. The cylinder was taken out of the refrigerator and the top layer was decanted and centrifuged repeatedly with fresh media for fifteen minutes at 3600 RPM. Similarly, the solid portion at the bottom of the cylinder was also centrifuged. The cloudy portion of the broth was centrifuged repeatedly until most of the solid remained at the bottom of the centrifuge tubes.

The solid pellets at the bottom of the centrifuge tubes were mixed with the recycled glass beads (lot #01-129). The glass beads were then placed in the SCFE sampling holder to be extracted. The SCFE was set up for 40° C., 20 g of carbon dioxide/min., and 400 bar. The run was extended for six hours and 9.45 g of semi-solid was collected. The semi-solid was powdery in nature initially and slightly yellow in color. The sample bottle was labeled extract #1, Lot #R011002 (Semisolid). The semi-solid was further divided into liquid (l), ~4.5 g, and solid(s), ~4.5 g, by separation of the liquid and the solid from the semisolid. The SCFE was set up again under the same conditions. The sample holder with the beads was taken out and 100-ml of methanol was placed inside the vessel to be used as the cosolvent. The run lasted for one hour. It was performed to clean the SCFE system and 71 ml of sample was collected. The initial sample was yellow and the later samples were then clear.

The SCF system was set up at 20 g of carbon dioxide/min for 40° C. and 375 bar. The system, also integrated with a solvent pump (HPLC), was set at different flow rates of methanol (mL/min). Samples were taken from different rates of methanol flow. Each sample was labeled MeOH fraction #1, MeOH fraction #2, and so on. If the sample went over 100 ml, another sample bottle was started. These samples obtained under the same conditions were labeled as MeOH fraction #7A, MeOH fraction #7B, and so on. The vessel pressure was maintained at 375 bar unless otherwise specified. If the co-solvent pump was not utilized, then it was marked as 'No pump' under the 'Flow' section. Collected samples are identified as given in Table 6. All samples were analyzed by HPLC to determine the quantity of geldanamycin. The results are presented in Table 6.

The extracted solvent samples were filtered with 0.2μm nylon filter and the filtrate collected in a separate container. Solids were collected in a separate container and labeled as geldanamycin #1 (R011002-1). Approximately 16 mg of product was recovered. The geldanamycin was yellow in color and it was placed under vacuum using a desiccator. The filtrate was distilled to remove methanol using a rotary device. The rotavap bath temperature was maintained between 20° C. and 25° C. About 1730 ml of the filtrate was distilled to recover the product. The methanol was distilled until the solution turned into slurry. The slurry was then placed in the refrigerator for one hour and was then filtered. The solid was collected and labeled as geldanamycin #2 (R0111002-2). Nearly 298.9 mg was collected in all and the product appeared as a fine yellow powder. The product was placed under vacuum for continued drying. The filtrate was placed in the freezer overnight and was filtered again to recover the crystals formed during storage. Nearly 72.2 mg of additional yellow colored product was recovered. The sample was labeled geldanamycin #3 (R011002-3) and placed under vacuum. The methanol from the filtrate was distilled again until it was about 20 ml. The slurry was placed in the freezer for two hours and the slurry was filtered to recover additional solids. About 92 mg of product was collected and it was a darker yellow in color. The sample was labeled geldanamycin #4 (R011002-4) and placed under vacuum overnight for drying at room temperature. The different amounts of product collected were as follows: R011002-1, 16 mg; R011002-2, 299 mg; R011002-3, 72 mg; R01002-4, 92 mg.

All samples were analyzed by HPLC to determine the purity of geldanamycin. The results are presented in Table 7. The purity of the product was improved significantly and it differed depending on the stage of collection. The product was further characterized by FTIR, TGA, and DSC. The data indicated that the product obtained was similar to that of the standard geldanamycin data provided by NCI.

Example: Selective SCF Extraction Geldanamycin from Fermentation Broth and Continued Integration of Co-solvent Pump. One liter of the geldanamycin broth (lot #01-139) was poured into a 1000-mL beaker. The broth was centrifuged at 3600 RPM for fifteen minutes. The supernatant was placed into a separate container. The pellet was left at the bottom of the centrifuge tube. The broth was centrifuged over and over again until most of the liquid was separated from the solid.

The solid (pellet) at the bottom of the centrifuge tubes was mixed with glass beads. The glass beads were then placed in the sample holder of the SCFE. The SCFE was set up for 375 bar, 40° C., and 20 g/min. The first run was done with no co-solvent and continued for five hours. The sample was a white to yellow semi-solid and about 4 grams was collected. The sample was labeled extract #1 (R011100 Semisolid) and submitted for analysis. The SCFE was run again under the same conditions for another four hours followed by another two hours. No additional semi-solid was recovered. The glass beads along with the solids were taken out and 100 mL of methanol poured in. The run lasted one hour and 75 mL of sample was collected. The initial sample was yellow and later samples were clear. The run was performed to clean the SCFE. The sample was labeled R011100 MeOH cleaning (R011100 MeOH Extraction Wash).

The SCFE was set up again for 40° C., 375 bar, 20 g of carbon dioxide/min., and 2.0 mL of methanol/min. Samples were collected every ten minutes. The pressure was maintained at 375 bar and 20 g of carbon dioxide/min for all runs with or without the use of the co-solvent pump. During extraction #7 the containers were washed with methanol and the washings were added to the SCF extraction vessel to recover any product sticking to the surface. All samples were analyzed by HPLC to determine the quantity of geldanamycin. The results are presented in Table 8.

The MeOH samples were then filtered through 0.2 μm nylon filter. The collected product was labeled as geldanamycin #1 (R011100). The solid was bright yellow and about 24 mg was recovered. The sample was placed under the vacuum desiccator for drying.

The filtrate of 680 mL was distilled using a rotary device. The filtrate was distilled to slurry and placed in the freezer (−20° C.) for two hours. The slurry was then filtered and solid product was collected and labeled as geldanamycin #2 (R011100). Nearly 134 mg was collected and the solid was bright yellow. The left over filtrate was placed in the freezer for further processing. The product recovered was as follows: R011100-1, 24 mg; R011100-2, 134 mg.

All samples were analyzed by HPLC to determine the quantity of geldanamycin. The results are presented in Table 9. The results show that the product recovered continued to be of high purity.

Example: SCF Extraction of Geldanamycin from Fermentation Broth Using a Co-solvent Pump. One liter of the broth (MPI Lot #01-139) was poured into a one-liter beaker. The broth was centrifuged at 3600 RPM for fifteen minutes. The solid pellets were left at the bottom of the tubes while the supernatant was placed into another container. The broth was centrifuged repeatedly until the solid was separated from the liquid.

The solid pellet at the bottom of the centrifuge tube was mixed with glass beads. The glass beads containing the solids were placed in the SCFE. The first run was done with no co-solvent at 400 bar, 20 g of carbon dioxide/min at 40° C. for four hours. Nearly 4.07 g of solid sample was collected. The sample was labeled as (R011102) extract #1. It was eventually separated into semisolid and liquid portions since it contained both. The liquid was labeled (R011102 semisolid #2 liquid) while the solid was labeled (R011102 semisolid #1 solid). The liquid contained 1.396 g while the solid contained 2.67 g of material. The beads were then taken out and a MeOH wash was done with 100 mL of MeOH. The run lasted one hour and 70 mL of sample was collected. The samples were yellow at first and then turned clear. The sample was labeled (R011102 MeOH extraction wash).

The SCFE was set at 400° C., 375 bar, and 30 g carbon dioxide flow/min. Glass beads were placed back in the vessel and performed SCFE for one hour without any co-solvent and another 0.6 grams of semisolid was collected.

The co-solvent pump was then set to run at for 9.0 mL/min and the extraction continued under the above conditions. Approximately 100 mL of the sample was collected in each bottle before starting a new bottle. However, the initial 19 mL was collected separately. By the end of #9, 734 mL of sample was recovered using 800 mL of MeOH for extraction.

The SCFE was then set at 40° C., 375 bar, and 20 g of carbon dioxide flow/min. and 100 mL of MeOH (including the MeOH used to rinse the beakers and tubes) was used as the co-solvent for each run. The runs lasted 45 minutes each. The runs were repeated until the sample was almost clear. All samples were analyzed by HPLC to determine the quantity of geldanamycin. The results are presented in Table 10.

All extracted MeOH samples from #3 to #16 were filtered through 0.2 μm nylon filter. No solid was collected on filtration. There was a total of 1130 mL filtrate. The filtrate was distilled using a rotavap, which was maintained between 20° C. and 25° C., until the solution became slurry. The slurry was kept in the freezer for 1 hour. MeOH extraction #2 was also filtered through 0.2 μm nylon filter, which did not yield any product. A fresh filter was placed on the filtration apparatus to filter the slurry that was kept in the freezer. About 168 mg of yellow colored product was collected and labeled as geldanamycin #1 (R011102). Extraction #2 filtrate was also distilled along the left out filtrate to slurry.

The slurry was placed in the freezer for one hour. It was filtered and 105 mg of product was recovered, which was dark yellow in color. The product was labeled as geldanamycin #2 (R011102). Both samples were placed in a vacuum desiccator for drying at room temperature. The final filtrate was not further processed. Both samples were re-weighed and geldanamycin #1 contained 168 mg while Geldanamycin #2 contained 99 mg. The product weights were as follows: R011102-1, 168 mg; R011102-2, 99 mg.

All samples were analyzed by HPLC to determine the quantity of Geldanamycin. The results are presented in Table 11. The purity of the compound was above 95%, but varied depending on the stage of separation.

Example: Selective SCF Extraction of Geldanamycin from Fermentation Broth. Two liters of the fermentation broth (MPI lot #: 01-235) was poured into two separate one-liter beakers. The broth was allowed to settle for two days. The tubes were filled to the 35-mL mark and then centrifuged for fifteen minutes at 3600 RPM. The broth was then centrifuged until all the solids were separated from the liquid. All the solids were collected in two tubes.

The solids (pellets) in the two tubes were mixed with glass beads. The SCFE was set up for 400 bar, 20 g/min., and 40° C. The glass beads were put into the holding vessel and the SCFE was started and run for six hours. The sample was fluffy, white, and yellow in nature and 8.737 g material was collected. The solid portion was separated from the liquid and 1.158 g of it turned into liquid and 7.579 g of sample remained as solid. The samples were labeled (/R011209 Semisolid #1 solid) and (/R011209 Semisolid #2 liquid). A MeOH wash was set up by taking the glass beads out and by adding 100 mL of MeOH to the SCFE. The run lasted for one hour and 77 mL of sample was collected. The sample was yellow at first, and then clear at the end. The sample was labeled as Extraction wash (R011209 MeOH Extraction Wash).

The SCFE was set up at 375 bar, 40° C., and 20 g of carbon dioxide/min. The glass beads were placed back in the sample holder. The 1000-mL beakers and centrifuge tubes were rinsed with approximately 15-mL of MeOH, which was used as co-solvent for the first run. Nearly 15 mL of sample was collected, which was cloudy in appearance and yellow in color. The sample was labeled as R011209 MeOH extraction #1. For extractions up to #8, 100-mL of MeOH was used as the co-solvent for the subsequent runs and extractions were conducted until samples appeared clear.

The co-solvent pump was started at 6.0 mL of MeOH/min. The pressure was also changed to 350 bar, 40° C. and the flow was changed to 30 g of carbon dioxide/min. Samples were collected up to #12, which was clear.

The co-solvent pump was then turned off. The SCFE was set at 375 bar and 20 g carbon dioxide/min and two additional runs up to #14 were performed. All samples were analyzed by HPLC to determine the quantity of geldanamycin. The results are presented in Table 12.

All samples were filtered with 0.2 μm nylon filter. The resulting filtrate was then distilled into slurry and kept in the freezer for 15 minutes. The slurry was filtered to collect the solid. Filtered the slurry and collected 367 mg of bright yellow compound. The compound was labeled as geldanamycin #1 (R011209) and placed under vacuum in the desiccator. The filtrate was placed in the freezer overnight.

The filtrate was distilled into slurry, which was then filtered. No further solid was recovered. The final product recovered from R011209 weighed 367 mg.

All samples were analyzed by HPLC to determine the quantity of geldanamycin. The results are presented in Table 13. The product obtained was approximately 98% pure. Additional characterization including FTIR, TGA, and DSC revealed that the purified product was similar to that of the standard reference geldanamycin.

In the foregoing examples, certain standard materials and procedures were employed, and are described immediately below.

Supercritical Fluid Extraction System. The composite PC-controlled Supercritical Fluid Extraction System device has several components (high-pressure pump, extraction vessel, back pressure regulator, and analyte collection vessel) besides the source of solvent (e.g., $CO_2$). A high pressure pump was used for supercritical fluids. The pump is capable of control based on feedback from a pressure/flow sensor. The pump is controlled using a programmable display or RS232C interface via PC. The pump can be used up to a flow rate of up to 200 grams/minute and pressure up to 680 bar at ambient temperature. Pump head is cooled internally by circulating coolant through the grooved path inside the head. It is also equipped with pressure sensor for maximum pressure setting and pressure gauge for viewing. It can pump liquid $CO_2$ under pressure or equation flow control. A cooling bath is attached to circulate coolant through the pump heads. In addition, there is a pre-cooler, which is a coiled heat exchanger used to cool the $CO_2$ before it enters the pump. A "finger tight" high-pressure vessel is designed for simple opening and closing. The vessel utilizes graphite reinforced Teflon™ "c" cup type seal with an energized spring. Tile energized spring under pressure forces the inner lip to contact the surface of the threaded cap and outer lip to contact inner vessel wall thus preventing the cap from being opened. Caps at each end of the vessel, along with a seal, have a frit assembly to provide even distribution of fluid during introduction. Threaded cap design with spring loaded seal not only enhances safety, but also lends to automation for efficient loading and unloading of large vessels. The 1-liter vessel was made of 17-4-PH stainless steel. The amount of material loading is determined based on the bulk density of the matrix for extraction. The vessel can bold the pressure up to 680 bar and temperature up to 100° C. It has a heating jacket to control the extraction temperature. A heating bath is used to circulate heated fluid through the heating jacket of the extraction vessel for temperature control. The bath is controlled via PC. In addition, there is a pre-heater, which is a coiled heat exchanger to heat the $CO_2$ entering the heated vessel. There is also in the vessel a basket, which is necessary when a product must avoid contact with the surface of the vessel wall. A basket avoids possible cross-contamination. A back pressure regulator was used to control back pressure. The back pressure regulator has built-in heating to compensate for any freezing due to pressure drop and has sapphire/high strength stainless steel seats to tackle any erosion problems. A built in pressure sensor provides closed loop feedback for control of the back pressure regulator. It can handle a flow rate of up to 200 grams/min and pressure up to 680 bar and can be heated to 100° C. A high-pressure 200 mL collection vessel served as a collection means. The fluid is introduced tangentially at high velocity into the chamber of the cyclone separator. Centrifugal forces act on the heavier particles forcing them to the inner wall of the separator and allowing the lighter particles to exit through a center tube. The bottom is tapered to provide efficient collection of separated material. It is made of high strength stainless steel and can with stand up to 100 bar pressure. It has a needle valve at the bottom to facilitate collection. The set-up also had a manual high-pressure valve for additional control. Relief valves and rupture discs are appropriately placed in the system for safety due to high-pressure operation.

Chemical Extraction of Geldanamycin from Fermentation Broth. The purpose of this effort was to determine the actual quantity of geldanamycin present in the fermentation broth by organic solvent extraction. A description of the procedure follows: 1. Shake the broth sample thoroughly to mix solids with the liquid portion of the sample to obtain a uniform dispersion. 2. Immediately (before solids settle) remove 2.0 mL of broth using a 5-mL disposable, glass graduated pipette with tip cut off to allow solids to enter, and place into a disposable glass tube with screw-cap. Prepare sample in triplicate. 3. Add 0.5 gram NaCl to each tube, cap and shake well. 4. Add 3 mL of ethyl acetate to each tube. Cap and shake well. 5. Centrifuge, if necessary, to settle the emulsion. 6. Remove clear supernatant and place into another glass tube, leaving any emulsion behind. 7. Repeat steps 5, 6, and 7, combining this clear supernatant with the first. 8. Place tubes containing the ethyl acetate extract into the SPE vacuum chamber and apply vacuum to evaporate the ethyl acetate to dryness. 9. Reconstitute the dried sample with 2 mL of methanol. Vortex well to dissolve the residue. 10. Syringe-filter the reconstituted sample extract through a 0.45 $\mu$m nylon filter into an autosampler vial. Alternatively, the extract may be micro-centrifuged and the supernatant transferred to an autosampler vial. 11. Analyze samples and standard solutions (prepared in methanol, ranging in concentration from approximately 650 $\mu$g/mL to approximately 25 $\mu$g/mL) by HPLC/DAD. The HPLC analysis revealed that the amount of geldanamycin present was ranged from about 300 to about 400 mg/L of broth. The supernatant free of solids) contained insignificant amount of the compound.

Analysis of Geldanamycin Final Products by Thin Layer Chromatography. Geldanamycin reference standard is dissolved in methanol to form a solution with a concentration of approximately 600 $\mu$g/mL. Samples of geldanamycin final products were prepared by dissolving sufficient material in methanol to form a solution of approximately 600 $\mu$g/mL. Equal amounts (approximately three drops applied with a glass capillary) of sample and standard solutions are spotted onto the plate origin and allowed to dry. Plate: Whatman Al Sil G/UV 250 $\mu$m Silica Gel (Catalog No. 4420 222). Solvent System: 9:1 Methylene Chloride: Methanol. Detection: Short wavelength ultraviolet and phosphomolybdic acid reagent. Rf for geldanamycin: approximately 0.76.

Analysis of Geldanamycin Final Products Using FTIR. Two to three mg of final product were transferred to a mortar and crushed to a fine powder with a pestle. Potassium bromide (200–300 mg) was added and mixed until a uniform mixture was obtained. A small aliquot of the mixture was placed into a dye press and transparent pellet was created. The pellet was then analyzed by FTIR. Instrument: Perkin Elmer Spectrum 1000. Scan Range: 400–4400 wavenumbers.

HPLC Analysis of Geldanamycin Samples. Geldanamycin standard solutions were prepared from reference standard material provided by NCI. A stock solution was prepared at about 650 $\mu$g/mL in methanol. This solution was further diluted with methanol to form working standard solutions in the range of about 20 $\mu$g/mL to about 650 $\mu$g/mL. Geldanamycin broth samples were extracted per standard extraction procedure. The final extracts were analyzed concurrently with working standards for quantitation. Geldanamycin supercritical extractions in methanol were analyzed directly. These samples were filtered or centrifuged to remove particulates as necessary. In the case of geldanamycin semisolids, approximately 250 mg of sample were weighed into a small test tube. Two mL of methanol were added to the tube. The test tube was placed into a sonication bath and left for about 15 minutes. The solution was filtered or centrifuged before being transferred to an autosampler vial for analysis by HPLC/DAD. Samples of geldanamycin final products were prepared as described for reference standards. Sample and standard solutions were injected concurrently on a HPLC chromatograph with a Diode Array Detector (DAD), according to the following parameters: Instrumentation: Hewlett Packard Model 1100, or equivalent; Column: Varian Microsorb, 100×4.6 mm, 5 $\mu$m; Mobile Phase: 55:45 (v/v) ACN:H$_2$O; Detector: Diode Array Detector (DAD) at 254 nm; Flow Rate: 0.5 mL/min; Injection Volume: 10.0 $\mu$L; Run Time: 10 minutes; Autosampler temperature: 4° C.; Column temperature: Ambient. The concentrations of Geldanamycin in the sample preparations were calculated by applying the peak areas for the Geldanamycin peak in the sample preparations to the equation for the best-fit line constructed from a graph of standard concentrations versus Geldanamycin peak areas. This value was reported directly for liquid samples and for broth extraction samples. Percent purity for the final products were calculated as follows: Purity %=Determined Concentration× 100%/Theoretical Concentration. Geldanamycin concentrations in semisolid samples were calculated as follows: ppm=($\mu$g/mL of sample solution)*(Dilution volume mL)/ (weight of sample in grams).

Example: Process including SCF and organic solvent extractions. Particulate matter from a fermentation broth of an organism that produces a benzoquinoid ansamycin is extracted using SCF as in any of the foregoing Examples. The extract is separated into benzoquinoid ansamycin crystals and a first other material by crystallization of a portion of the benzoquinoid ansamycin in the extract. However, some benzoquinoid ansamycin remains in the first other material. The first other material is then concentrated by distillation to a state that may have the consistency of glue or be described as semisolid. The semisolid is extracted again using SCF as in any of the foregoing Examples. The SCF extract is separated into benzoquinoid ansamycin crystals and a second other material by crystallization of a portion of the benzoquinoid ansamycin in the extract. Some benzoquinoid ansamycin remains in the second other material. Benzoquinoid ansamycin remaining in the first other material or the second other material or both is extracted from the material by the use of an organic solvent system such as chloroform/methanol.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can fairly, legally and equitably be accorded to the appended claims.

TABLE 1

SCF Extraction and Estimation of Geldanamycin Present in Fermentation Broth

| Description | Extraction Method | Recovery | Sample Conc. (ug/mL) | ~mg* |
|---|---|---|---|---|
| EtOH 1 | 20 g/min., 200 bar, 100 ml EtOH | NA | 374.6 | NA |
| EtOH 2 | 20 g/min., 400 bar, 100 ml EtOH | NA | 348.9 | NA |

TABLE 1-continued

SCF Extraction and Estimation of Geldanamycin Present in Fermentation Broth

| Description | Extraction Method | Recovery | Sample Conc. (ug/mL) | ~mg* |
|---|---|---|---|---|
| EtOH 3 | 20 g/min., 400 bar, 100 ml EtOH | NA | 169.4 | NA |
| R010807 EtOAc #2 | Chemical/ Conventional | NA | 126.9 | NA |
| R010807 #1A, MeOH | 20 g/min., 400 bar, 100 ml MeOH | 56 ml | 671.4 | 37.6 |
| R010807 #2A, MeOH | 20 g/min., 400 bar, 100 ml MeOH | 58 ml | 323.4 | 18.8 |
| R010807 #3A, MeOH | 20 g/min., 400 bar, 100 ml MeOH | 56 ml | 101.3 | 5.7 |
| R010807 #4A, MeOH | 20 g/min., 400 bar, 100 ml MeOH | 58 ml | 46.8 | 2.7 |
| R010807 EtOAc #1 | Chemical/ Conventional | NA | 6.1 | NA |
| R010807 #1, MeOH | 20 g/min., 400 bar, 100 ml MeOH | 59 ml | 868.1 | 51.2 |
| R010807 #2, MeOH | 20 g/min., 400 bar, 100 ml MeOH | 51 ml | 439.7 | 22.4 |
| R010807 Sup #1 | Chemical/ Conventional | NA | 0.9 | NA |

*Approximate amount of Geldanamycin present in the samples.
NA - Not Applicable or Not Determined

TABLE 2

SCF Extraction and Estimation of Geldanamycin Present in Fermentation Broth

| Description | Extraction Method | Recovery | Sample Conc. (ug/mL) | ~mg* |
|---|---|---|---|---|
| R010904 Semisolid | 20 g/min., 400 bar | 1.49 g | 554 ppm | 0.8 |
| R010904 #2, MeOH | 20 g/min., 400 bar, 100 ml MeOH | 60 ml | 27.7 | 1.7 |
| R010904 #3, MeOH | 20 g/min., 400 bar, 100 ml MeOH | 70 ml | 1153.9 | 80.8 |
| R010904 #4, MeOH | 20 g/min., 400 bar, 100 ml MeOH | 55 ml | 674.6 | 37.1 |
| R010904 #5, MeOH | 20 g/min., 400 bar, 100 ml MeOH | 76 ml | 737.0 | 56.0 |
| R010904 #6, MeOH | 20 g/min., 400 bar, 100 ml MeOH | 76 ml | 393.6 | 29.9 |
| R010904 #7, MeOH | 20 g/min., 400 bar, 100 ml MeOH | 66 ml | 125.1 | 8.3 |
| R010904 #8, MeOH | 20 g/min., 400 bar, 100 ml MeOH | 61 ml | 165.4 | 10.1 |
| R010904 #9, MeOH | 20 g/min., 400 bar, 100 ml MeOH | 82 ml | 22.3 | 1.8 |
| R010904 #10, MeOH | 20 g/min., 400 bar, 100 ml MeOH | 68 ml | 1219.4 | 82.9 |
| R010904 #11, MeOH | 20 g/min., 400 bar, 100 ml MeOH | 46 ml | 331.6 | 15.3 |
| R010904 #12, MeOH | 20 g/min., 400 bar, 100 ml MeOH | 74 ml | 61.5 | 4.6 |
| R010904 #13, MeOH | 20 g/min., 400 bar, 100 ml MeOH | 81 ml | 14.5 | 1.2 |

TABLE 2-continued

SCF Extraction and Estimation of Geldanamycin Present in Fermentation Broth

| Description | Extraction Method | Recovery | Sample Conc. (ug/mL) | ~mg* |
|---|---|---|---|---|
| R010904 Sup #1 | Chemical/ Conventional | NA | 9.0 | NA |
| R010904 Sup #2 | Chemical/ Conventional | NA | 98.7 | NA |

*Approximate amount of Geldanamycin present in the samples.
For each batch extraction with 100 ml MeOH addition, the run lasted one hour.
MeOH samples were centrifuged before HPLC analysis.
Sup#1 is the supernatant after centrifugation.
Sup#2 Supernatant mixed with some solid mass that could not be separated by centrifugation.
NA = Not Applicable or Not Determined.

TABLE 3

Purity Determination of Crystallized Geldanamycin by HPLC

| Sample ID | Trial # | Theoretical Conc. ug/mL | Determined Conc. ug/mL | Percent Purity | Average % Purity | Adjusted % Purity* |
|---|---|---|---|---|---|---|
| R010807, R010904-1 | 1 | 628 | 606.8 | 96.6 | 96.6 | NA |
| R010807, | 5A | 97 | 44 | 45.4 | | NA |
| R010904-2 | 5B | 98 | 41.9 | 42.8 | 44.1 | NA |
| R010807, | 6A | 99 | 68 | 68.7 | | NA |
| R010904-3 | 6B | 105 | 69.8 | 66.5 | 67.6 | NA |
| R010807, | 7A | 105 | 14.7 | 14 | | NA |
| R010904-4 | 7B | 109 | 12.8 | 11.7 | 12.9 | NA |
| R010807, | 8A | 99 | 38.5 | 38.9 | | NA |
| R010904-5 | 8B | 97 | 46.3 | 47.7 | 43.3 | NA |
| Filtrate 1 R010807, R010904 | 1 | NA | 7758 ppm** | NA | NA | NA |

*Purity was not adjusted based on reference standard.
**ppm = 1618.4 μg/ml × 1 ml/0.2086 g. Total mass of sample = 1.0498 g. Therefore total geldanamycin in sample = 8144 μg.
NA = Not Applicable or Not Determined.

TABLE 4

SCF Extraction and Estimation of Geldanamycin Present in Fermentation Broth

| Description | Extraction Method | Recovery | Sample Conc. (ug/mL) | ~mg* |
|---|---|---|---|---|
| R011001 Semisolid 1A | 20 g/min., 400 bar | 2.8 g | 747.6 ppm** | NA |
| R011001 Semisolid 1B | NA | NA | 936.1 ppm*** | 2.4 (avg.) |
| MeOH 2 | 20 g/min., 400 bar, 100 ml MeOH | 77 ml | 20.6 | 1.6 |
| MeOH 3 | 20 g/min., 400 bar, 100 ml MeOH | 86 ml | 1249 (d) | 107.4 |
| MeOH 4 | 20 g/min., 400 bar, 100 ml MeOH | 64 ml | 817.8 (d) | 52.3 |
| MeOH 5 | 20 g/min., 400 bar, 100 ml MeOH | 78 ml | 823.2 (d) | 62.2 |
| MeOH 6 | 20 g/min., 400 bar, 100 ml MeOH | 71 ml | 957.0 (d) | 68.0 |
| MeOH 7 | 20 g/min., 400 bar, 100 ml MeOH | 81 ml | 731.0 (d) | 59.2 |

TABLE 4-continued

SCF Extraction and Estimation of Geldanamycin Present in Fermentation Broth

| Description | Extraction Method | Recovery | Sample Conc. (ug/mL) | ~mg* |
|---|---|---|---|---|
| MeOH 8 | 20 g/min., 400 bar, 100 ml MeOH | 82 ml | 474.7 | 38.9 |
| MeOH 9 | 20 g/min., 400 bar, 100 ml MeOH | 90 ml | 523.7 | 47.1 |
| MeOH 10 | 20 g/min., 400 bar, 100 ml MeOH | 88 ml | 637.8 | 56.1 |
| MeOH 11 | 20 g/min., 400 bar, 100 ml MeOH | 92 ml | 317.3 | 29.2 |
| MeOH 12 | 20 g/min., 400 bar, 100 ml MeOH | 85 ml | 285.2 | 24.2 |
| MeOH 13 | 20 g/min., 400 bar, 100 ml MeOH | 92 ml | 231.4 | 21.3 |
| MeOH 14 | 20 g/min., 400 bar, 100 ml MeOH | 88 ml | 139.1 | 12.2 |
| MeOH 15 | 20 g/min., 400 bar, 100 ml MeOH | 86 ml | 256.4 | 22.1 |
| MeOH 16 | 20 g/min., 400 bar, 100 ml MeOH | 90 ml | 208.2 | 18.7 |
| MeOH 17 | 20 g/min, 400 bar, 100 ml MeOH | 89 ml | 202.7 | 18.0 |
| MeOH 18 | 20 g/min., 400 bar, 100 ml MeOH | 86 ml | 128.7 | 11.1 |
| MeOH 19 | 20 g/min., 400 bar, 100 ml MeOH | 77 ml | 84.8 | 6.5 |
| MeOH 20 | 20 g/min., 400 bar, 100 ml MeOH | 86 ml | 256.5 | 22.1 |
| MeOH 21 | 20 g/min., 400 bar, 100 ml MeOH | 87 ml | 66.8 | 5.8 |
| MeOH 22 | 20 g/min., 400 bar, 100 ml MeOH | 71 ml | 95.5 | 6.8 |
| Cleaning Sample | 20 g/min., 400 bar, 100 ml MeOH | 61 ml | trace | NA |
| Osmotic Distillation S2 | NA | ~60 ml | 40.7 | 2.4 |
| Osmotic Diss. 1 | 20 g/min., 375 bar, no MeOH | 2 ml | 124.3 | 0.2 |
| Osmotic Diss. 2 | 20 g/min., 375 bar, 100 ml MeOH | 80 ml | 37 | 3.0 |
| Osmotic Diss. 3 | 20 g/min., 375 bar, 100 ml MeOH | 75 ml | 16.3 | 1.2 |

*Approximate amount of Geldanamycin present in the samples.
For each batch extraction with 100 ml MeOH addition, the run lasted one hour.
MeOH samples were injected directly before analysis.
**ppm = 85.9 ug/mL × 2.0 mL / 0.229 g.
***ppm = 105.4 ug/mL × 2.0 mL / 0.2252 g.
(d) = sample diluted for analysis due to calibration range limitation.
Semi-solid was extracted with carbon dioxide alone for two hours.
NA = Not Applicable or Not Determined.

TABLE 5

Purity Determination of Crystallized Geldanamycin by HPLC

| Sample ID | Trial # | Theoretical Conc. ug/mL | Determined Conc. ug/mL | Percent Purity | Average % Purity | Adjusted* % Purity |
|---|---|---|---|---|---|---|
| R011001-1 | 1A | 100 | 84.6 | 84.6 | | NA |
| | 1B | 109 | 88.7 | 81.4 | 83 | NA |
| R011001-2 | 2A | 102 | 85.9 | 84.2 | | NA |
| | 2B | 105 | 91.5 | 87.1 | 85.7 | NA |
| R011001-3 | 3A | 108 | 71.3 | 66 | | NA |
| | 3B | 104 | 65.7 | 63.2 | 64.6 | NA |
| R011001-4 | 4A | 111 | 9.3 | 8.4 | | NA |
| | 4B | 99 | 9.7 | 9.8 | 9.1 | NA |
| Filtrate 2, R011001 | 1 | NA | 6026** | NA | NA | NA |

*Purity was not adjusted based on reference standard.
**This sample diluted 5 fold before analysis. The sample concentration shown accounts for dilution
NA = Not Applicable or Not Determined.

TABLE 6

SCF Extraction and Estimation of Geldanamycin Present in Fermentation Broth

| Sample Description | Extraction Method | Recovery | Concentration ug/ml | ~mg* |
|---|---|---|---|---|
| Semisolid (1) S3 | 20 g/min., 375 bar | ~4.75 g | 28.1 ppm** | NA |
| Semisolid (1) S4 | NA | NA | 15.6 ppm** | 0.1 (avg.) |
| Semisolid (s) S5 | NA | ~4.75 g | 1413.2 ppm** | NA |
| Semisolid (s) S6 | NA | NA | 1422.3 ppm** | 6.7 (avg.) |
| MeOH Extraction 1 | 20 g/min. 0.40 ml/min., 375 bar | 8 ml | 274.7 | 2.2 |
| MeOH Extraction 2 | 20 g/min., 0.80 ml/min., 375 bar | 10 ml | 225.5 | 2.3 |
| MeOH Extraction 3 | 20 g/min., 1.60 ml/min., 375 bar | 37 ml | 151.0 | 5.6 |
| MeOH Extraction 4A | 20 g/min., 3.20 ml/min., 375 bar | 85 ml | 201.2 | 17.1 |
| MeOH Extraction 4B | 20 g/min., 3.20 ml/min., 375 bar | 110 ml | 189.6 | 20.9 |
| MeOH Extraction 4C | 20 g/min., 3.20 ml/min., 375 bar | 73 ml | 180.2 | 13.2 |
| MeOH Extraction 5 | 20 g/min., 400 bar, 100 ml of MeOH | 92 ml | 990.2*** | 91.1 |
| MeOH Extraction 6 | 20 g/min., 1.60 ml/min., 375 bar | 39 ml | 831.0*** | 32.4 |
| MeOH Extraction 7A | 20 g/min., 2.0 ml/min., 375 bar | 103 ml | 437.5 | 45.1 |
| MeOH Extraction 7B | 20 g/min., 2.0 ml/min., 375 bar | 97 ml | 247.4 | 24.0 |

TABLE 6-continued

SCF Extraction and Estimation of Geldanamycin Present in Fermentation Broth

| Sample Description | Extraction Method | Recovery | Concentration ug/ml | ~mg* |
|---|---|---|---|---|
| MeOH Extraction 7C | 20 g/min., 2.0 ml/min., 375 bar | 97 ml | 265.6 | 25.8 |
| MeOH Extraction 7D | 20 g/min., 2.0 ml/min., 375 bar | 92 ml | 242.1 | 22.3 |
| MeOH Extraction 7E | 20 g/min., 2.0 ml/min., 375 bar | 100 ml | 236.8 | 23.7 |
| MeOH Extraction 7F | 20 g/min., 2.0 ml/min., 375 bar | 99 ml | 229.3 | 22.7 |
| MeOH Extraction 7G | 20 g/min., 2.0 ml/min., 375 bar | 101 ml | 217.6 | 22.0 |
| MeOH Extraction 7H | 20 g/min., 2.0 ml/min., 375 bar | 99 ml | 205.0 | 20.3 |
| MeOH Extraction 8 | 20 g/min., 400 bar, 100 ml of MeOH | 79 ml | 989.4** | 78.2 |
| MeOH Extraction 9 | 20 g/min., 400 bar, 100 ml of MeOH | 72 ml | 490.9 | 35.3 |
| MeOH Extraction 10A | 20 g/min., 2.0 ml/min., 375 bar | 104 ml | 527.9 | 54.9 |
| MeOH Extraction 10B | 20 g/min., 2.0 ml/min., 375 bar | 81 ml | 150.0 | 12.2 |
| MeOH Extraction 11 | 20 g/min., 375 bar, 100 ml MeOH | 110 ml | 760.1** | 83.6 |
| MeOH Extraction 12 | 20 g/min., 375 bar, 100 ml MeOH | 91 ml | 227.2 | 20.7 |
| MeOH Extraction 13 | 20 g/min., 375 bar, 100 ml MeOH | 76 ml | 322.7 | 24.5 |
| MeOH Extraction 14 | 20 g/min., 375 bar, 100 ml MeOH | 61 ml | 141.6 | 86 |
| MeOH Extraction 15 | 20 g/min., 375 bar, 100 ml MeOH | 75 ml | 103.9 | 7.8 |

*Approximate amount of Geldanamycin present in the samples.
**ppm = (ug/mL)(2.0 mL) sample size (g)
***Note: Sample was diluted with 5mL into 10 mL of MeOH.
Semi-solid was extracted with carbon dioxide alone for six hours.
For each batch extraction w/100 ml MeOH addition, the run lasted one hour.
MeOH samples were centrifuged before analysis.
NA = Not Applicable or Not Determined.

TABLE 7

Purity Determination of Crystallized Geldanamycin by HPLC

| Sample ID | Trial No. | Theoretical Conc. ug/mL | Determined Conc. ug/mL | Percent Purity | Average % Purity | Adjusted* % Purity |
|---|---|---|---|---|---|---|
| R011002-1 | 1 | 318.0 | 309.7 | 97.4 | 97.4 | 95.6 |
| R011002-2 | 1 | 324.0 | 344.6 | 106.4 | | |
| | 2 | 334.0 | 344.1 | 103.0 | 104.7 | 102.8 |
| R011002-3 | 1 | 328.0 | 328.1 | 100.0 | | |
| | 2 | 356.0 | 364.2 | 102.3 | 101.2 | 99.3 |
| R011002-4 | 1 | 318.0 | 103.3 | 32.5 | | |
| | 2 | 320.0 | 101.6 | 31.8 | 32.1 | 31.5 |

*For Lot No. R011002: Adjusted % purity = Average % Purity × 0.982 (the factor 0.982 is taken from the purity of the reference standard as determined by peak area percentage for the most concentrated standard solution).

TABLE 8

SCF Extraction and Estimation of Geldanamycin Present in Fermentation Broth

| Sample Description | Extraction Method | Recovery | Concentration (ug/ml) | ~mg* |
|---|---|---|---|---|
| R011100 Semisolid (Solid) | 375 bar, 20 g/min. | 4 g | 2840 ppm** | 11.4 |
| R011100 Semisolid (Liquid) | NA | 0 g | 0.0 | NA |
| R011100 MeOH Extraction Wash | 375 bar, 20 g/min., 100 ml MeOH | 75 ml | 64.9 | 4.9 |
| R011100 MeOH Extraction #1 | 375 bar, 2.0 ml/min. | 8 ml | 210.5 | 1.7 |
| R011100 MeOH Extraction #2 | 375 bar, 2.0 ml/min. | 97 ml | 266.7 | 25.9 |
| R011100 MeOH Extraction #3 | 375 bar, 2.0 ml/min. | 98 ml | 205.6 | 20.2 |
| R011100 MeOH Extraction #4 | 375 bar, 20 g/min., 100 ml MeOH | 82 ml | 420.4 | 34.5 |
| R011100 MeOH Extraction #5 | 375 bar, 20 g/min., 100 ml MeOH | 92 ml | 605.9 | 55.7 |
| R011100 MeOH Extraction #6 | 375 bar, 20 g/min., 100 ml MeOH | 90 ml | 282.0 | 25.4 |
| R011100 MeOH Extraction #7 | 375 bar, 20 g/min., 100 ml MeOH | 87 ml | 817.8** | 71.2 |
| R011100 MeOH Extraction #8 | 375 bar, 20 g/min., 100 ml MeOH | 85 ml | 251.6 | 21.4 |
| R011100 MeOH Extraction #9 | 375 bar, 20 g/min., 100 ml MeOH | 83 ml | 124.3 | 10.3 |

*Approximate amount of Geldanamycin present in the samples.
**Sample diluted two fold and analyzed with a separate standard curve (value corrected for dilution).
For each batch extraction with 100 ml MeOH addition, the run lasted one hour.
MeOH samples were centrifuged before analysis.
**Sample weight for solid = 250.1 mg ug/ml for solid = 355.18
**ppm = (ug/mL)(2.0 mL) sample size (g)
Semi-solid was extracted with carbon dioxide alone for five hours.
NA = Not Applicable or Not Determined.

TABLE 9

Purity Determination of Crystallized Geldanamyciny HPLC

| Sample ID | Trial No. | Theoretical Conc. ug/mL | Determined Conc. ug/mL | Percent Purity | Average % Purity | Adjusted* % Purity |
|---|---|---|---|---|---|---|
| R011100-1 | 1 | 392.0 | 370.6 | 94.5 | | |
| | 2 | 356.0 | 346.0 | 97.2 | 95.9 | 93.3 |
| R011100-2 | 1 | 632.0 | 637.9 | 100.9 | | |
| | 2 | 628.0 | 614.7 | 97.9 | 99.4 | 96.7 |

*Adjusted % Purity = Average % Purity × 0.973 (the factor 0.973 is taken from the purity of the reference standard as determined by peak area percentage for the most concentrated standard solution.

TABLE 10

SCF Extraction and Estimation of Geldanamycin Present in Fermentation Broth

| Description | Extraction Method | Recovery | Concentration (ug/ml) | ~mg* |
|---|---|---|---|---|
| R011102 Semisolid #1 (Solid) | 20 g/min., 400 bar | 2.7 g | 461.5 ppm | 1.2 |
| R011102 Semisolid #2 (Liquid) | NA | 1.4 g | 193.7 ppm | 0.3 |
| R011102 Semisolid #3 (Solid/Liquid) | NA | 0.6 g | 1018.0 ppm | 0.6 |
| R011102 MeOH Extraction Wash | 20 g/min., 375 bar, 100 ml MeOH | 70 ml | 21.7 | 1.5 |
| R011102 MeOH Extraction #1 | 30 g/min., 9.0 ml/min., 375 bar | 19 ml | 643.5 | 12.2 |
| R011102 MeOH Extraction #2 | 30 g/min., 9.0 ml/min., 375 bar | 89 ml | 454.5 | 40.5 |
| R011102 MeOH Extraction #3 | 30 g/min., 9.0 ml/min., 375 bar | 95 ml | 176.1 | 16.7 |
| R011102 MeOH Extraction #4 | 30 g/min., 9.0 ml/min., 375 bar | 106 ml | 211.3 | 22.4 |
| R011102 MeOH Extraction #5 | 30 g/min., 9.0 ml/min., 375 bar | 100 ml | 223.1 | 22.3 |
| R011102 MeOH Extraction #6 | 30 g/min., 9.0 ml/min., 375 bar | 103 ml | 200.6 | 20.7 |
| R011102 MeOH Extraction #7 | 30 g/min., 9.0 ml/min., 375 bar | 93 ml | 179.8 | 16.7 |
| R011102 MeOH Extraction #8 | 30 g/min., 9.0 ml/min., 375 bar | 95 ml | 204.7 | 19.5 |
| R011102 MeOH Extraction #9 | 30 g/min., 9.0 ml/min., 375 bar | 34 ml | 259.2 | 8.8 |
| R011102 MeOH Extraction #10 | 20 g/min., 375 bar, 100 ml MeOH | 80 ml | 554.8 | 44.4 |
| R011102 MeOH Extraction #11 | 20 g/min., 375 bar, 100 ml MeOH | 90 ml | 455.4 | 41.0 |
| R011102 MeOH Extraction #12 | 20 g/min., 375 bar, 100 ml MeOH | 84 ml | 287.9 | 24.2 |
| R011102 MeOH Extraction #13 | 20 g/min., 375 bar, 100 ml MeOH | 84 ml | 209.9 | 17.6 |
| R011102 MeOH Extraction #14 | 20 g/min., 375 bar, 100 ml MeOH | 75 ml | 437.2 | 32.8 |
| R011102 MeOH Extraction #15 | 20 g/min., 375 bar, 100 ml MeOH | 82 ml | 226.4 | 18.6 |
| R011102 MeOH Extraction #16 | 20 g/min, 375 bar, 100 ml MeOH | 84 ml | 72.0 | 6.0 |

*Approximate amount of Geldanamycin present in the samples.
Semi-solid was extracted with carbon dioxide alone for five hours.
For each batch extraction with 100 ml MeOH addition, the run lasted one hour.
MeOH samples were centrifuged before analysis.
NA = Not Applicable or Not Determined.

TABLE 11

Purity Determination of Crystallized Geldanamycin by HPLC

| Sample ID | Trial No. | Theoretical Conc. ug/mL | Determined Conc. ug/mL | Percent Purity | Average % Purity | Adjusted* % Purity |
|---|---|---|---|---|---|---|
| R011102-1 | 1 | 628.0 | 622.7 | 99.2 | | |
| | 2 | 620.0 | 617.1 | 99.5 | 99.3 | 96.7 |
| R011102-2 | 1 | 644.0 | 404.9 | 62.9 | | |
| | 2 | 624.0 | 394.5 | 63.2 | 63.0 | 61.3 |

*Adjusted % Purity = Average % Purity × 0.973 (the factor 0.973 is taken from the purity of the reference standard as determined by peak area percentage for the most concentrated standard solution)

TABLE 12

SCF Extraction and Estimation of Geldanamycin Present in Fermentation Broth

| Sample Description | Extraction Method | Recovery | Concentration (ug/ml) | ~mg* |
|---|---|---|---|---|
| R011209 Semisolid #1 (Solid) | 20 g/min., 400 bar | 7.6 g | 1815.3 ppm** | 13.8 |
| R011209 Semisolid #2 (Liquid) | NA | 1.2 g | 1.8 ppm** | 0.002 |
| R011209 MeOH Extraction Wash | 20 g/min., 400 bar, 100 ml MeOH | 77 ml | 12.5 | 1.0 |
| R011209 MeOH Extraction #1 | 20 g/min., 375 bar, 15 ml MeOH | 15 ml | 395.9 | 5.9 |
| R011209 MeOH Extraction #2 | 20 g/min., 375 bar, 100 ml MeOH | 95 ml | 1113.0** | 105.7 |
| R011209 MeOH Extraction #3 | 20 g/min., 375 bar, 100 ml MeOH | 76 ml | 885.0*** | 67.3 |
| R011209 MeOH Extraction #4 | 20 g/min., 375 bar, 100 ml MeOH | 79 ml | 956.0*** | 75.3 |
| R011209 MeOH Extraction #5 | 20 g/min., 375 bar, 100 ml MeOH | 89 ml | 614.6 | 54.7 |
| R011209 MeOH Extraction #6 | 20 g/min., 375 bar, 100 ml MeOH | 89 ml | 849.0*** | 75.6 |
| R011209 MeOH Extraction #7 | 20 g/min., 375 bar, 100 ml MeOH | 91 ml | 435.0 | 39.6 |
| R011209 MeOH Extraction #8 | 20 g/min., 375 bar, 100 ml MeOH | 87 ml | 285.6 | 24.9 |
| R011209 MeOH Extraction #9 | 20 g/min., 6.0 ml/min., 350 bar | 91 ml | 173.2 | 15.8 |
| R011209 MeOH Extraction #10 | 20 g/min., 6.0 ml/min., 350 bar | 107 ml | 134.6 | 14.4 |
| R011209 MeOH Extraction #11 | 20 g/min., 6.0 ml/min., 350 bar | 101 ml | 93.5 | 9.4 |
| R011209 MeOH Extraction #12 | 20 g/min., 6.0 ml/min., 350 bar | 104 ml | 78.9 | 8.2 |
| R011209 MeOH Extraction #13 | 20 g/min., 375 bar, No MeOH | 33 ml | 124.5 | 4.1 |
| R011209 MeOH Extraction #14 | 20 g/min., 375 bar, 100 ml MeOH | 94 ml | 109.4 | 10.3 |

*Approximate amount of Geldanamycin present in the samples.
For each batch extraction with 100 ml MeOH addition, the run lasted one hour.
MeOH samples were centrifuged before analysis.
NA = Not Applicable or Not Determined.
**ppm = (250.6 ug/ml)(2 ml)/(0.761 g).
***These extracts diluted 5 fold prior to analysis.
Semi-solid was extracted with carbon dioxide alone for six hours.

TABLE 13

Purity Determination of Crystallized Geldanamycin By HPLC

| Sample ID | Trial No. | Theoretical Conc. ug/mL | Determined Conc. ug/mL | Percent Purity | Average % Purity | Adjusted* % Purity |
|---|---|---|---|---|---|---|
| R011209-1 | 1 | 628.0 | 635.1 | 101.1 | | |
| | 2 | 616.0 | 616.4 | 100.1 | 100.6 | 97.9 |

*Adjusted % Purity = Average % Purity × 0.973 (the factor 0.973 is taken from the purity of the reference standard as determined by peak area percentage for the most concentrated standard solution)

I claim:

1. A process for purifying a benzoquinoid ansamycin antibiotic, said process comprising contacting a mixture comprising the antibiotic with a fluid comprising supercritical carbon dioxide.

2. The process of claim 1 wherein the mixture comprises a fermentation broth.

3. The process of claim 2 wherein the fermentation broth comprises *Streptomyces hygroscopicus, Streptomyces hygroscopicus* var. *geldanus, Streptomyces hygroscopicus* var. *geldanus* var. *nova*, or a product of the fermentation of *Streptomyces hygroscopicus, Streptomyces hygroscopicus* var. *geldanus*, or *Streptomyces hygroscopicus* var. *geldanus* var. *nova*.

4. The process of claim 1 wherein the fluid further comprises an aliphatic alcohol.

5. The process of claim 2 wherein the fluid further comprises an aliphatic alcohol.

6. The process of claim 3 wherein the fluid further comprises an aliphatic alcohol.

7. The process of claim 4 wherein the alcohol is methanol or ethanol.

8. The process of claim 5 wherein the alcohol is methanol or ethanol.

9. The process of claim 6 wherein the alcohol is methanol or ethanol.

10. The process of claim 1 wherein the antibiotic is geldanamycin.

11. The process of claim 2 wherein the antibiotic is geldanamycin.

12. The process of claim 3 wherein the antibiotic is geldanamycin.

13. The process of claim 4 wherein the antibiotic is geldanamycin.

14. The process of claim 5 wherein the antibiotic is geldanamycin.

15. The process of claim 6 wherein the antibiotic is geldanamycin.

16. The process of claim 7 wherein the antibiotic is geldanamycin.

17. The process of claim 8 wherein the antibiotic is geldanamycin.

18. The process of claim 9 wherein the antibiotic is geldanamycin.

19. A process for purifying a benzoquinoid ansamycin antibiotic from a fermentation broth that contains the antibiotic, said process comprising (a) separating the fermentation broth into a particulate phase and a liquid phase, and (b) extracting the antibiotic from the particulate phase, wherein the extracting is performed using a fluid comprising supercritical carbon dioxide.

20. The process of claim 19 wherein the fluid further comprises an aliphatic alcohol.

21. The process of claim 20 wherein the alcohol is methanol or ethanol.

22. The process of claim 21 wherein the antibiotic is geldanamycin.

23. The process of claim 20 wherein the separating comprises centrifugation, sedimentation, filtration, or settling.

* * * * *